United States Patent [19]

Esders et al.

[11] 4,241,178

[45] Dec. 23, 1980

[54] PROCESS AND COMPOSITION FOR THE QUANTIFICATION OF GLYCEROL ATP AND TRIGLYCERIDES

[75] Inventors: Theodore W. Esders, Webster; Charles T. Goodhue, Rochester, both of N.Y.

[73] Assignee: Eastman Kodak Company, Rochester, N.Y.

[21] Appl. No.: 867,641

[22] Filed: Jan. 6, 1978

Related U.S. Application Data

[63] Continuation-in-part of Ser. No. 715,797, Aug. 19, 1976, abandoned.

[51] Int. Cl.$^3$ .................. C12Q 1/28; C12Q 1/44; C12Q 1/48
[52] U.S. Cl. ........................... 435/15; 435/19; 435/28
[58] Field of Search ........... 195/99, 103.5 R, 103.5 U, 195/103.5 C; 435/15, 19, 25, 28

[56] References Cited

U.S. PATENT DOCUMENTS

| | | | |
|---|---|---|---|
| 2,888,385 | 5/1959 | Grandel | 195/67 |
| 2,981,606 | 4/1961 | Keston | 195/103.5 R |
| 3,092,465 | 6/1963 | Adams et al. | 435/14 |
| 3,168,448 | 2/1965 | Melcer et al. | 195/66 |
| 3,189,529 | 6/1965 | Yamada et al. | 195/62 |
| 3,262,863 | 7/1966 | Fukumoto et al. | 195/66 |
| 3,513,073 | 5/1970 | Mauvernay et al. | 195/62 |
| 3,703,591 | 11/1972 | Bucolo et al. | 195/103.5 R |
| 3,759,793 | 9/1973 | Stork et al. | 195/103.5 R |
| 3,862,009 | 1/1975 | Wahlefeld et al. | 195/103.5 R |
| 3,886,045 | 5/1975 | Meiattini | 195/103.5 C |
| 3,898,130 | 8/1975 | Komatsu | 195/103.5 R |
| 3,917,453 | 11/1975 | Milligan et al. | 195/103.5 C |
| 3,992,158 | 11/1976 | Przybylowicz et al. | 195/103.5 R |

FOREIGN PATENT DOCUMENTS 1322462 7/1973 United Kingdom .
1441642 7/1976 United Kingdom .

OTHER PUBLICATIONS

Chin et al., *Biochemical Medicine*, 7 (1973), 460.
Yamazaki et al., *Molecular and Cellular Biochemistry*, vol. 2, No. 1, (1973), 39–52.
Fukumoto et al., *J. Gen. Appli. Microbiol.*, 10, (1964), 257–265.
Barman, *Enzyme Handbook*, I, (1969), pp. 401–402.
Jacobs et al., *Archives of Biochemistry and Biophysics*, 88 (1960), pp. 250–255.
Koditschek et al., *J. of Bact.*, vol. 98, No. 3, (1969), pp. 1063–1068.

*Primary Examiner*—Esther M. Kepplinger
*Attorney, Agent, or Firm*—Torger N. Dahl

[57] ABSTRACT

A method is described for the assay of glycerol (as either free glycerol or a fatty acid ester of glycerol) in aqueous liquids such as blood serum. The method comprises the steps of
  I: contacting in the presence of an electron acceptor
    (a) a sample to be assayed and (b) a novel reagent composition comprising
      1. optionally, a lipase which hydrolyzes triglycerides to glycerol;
      2. glycerol kinase;
      3. adenosine triphosphate;
      4. α-glycerophosphate oxidase to produce a detectable change in the presence of triglyceride or a general positive sample; and
  II: detecting the occurrence of said detectable change.

The lipase is included when fatty acid esters of glycerol (i.e., triglycerides) are to be detected. Free glycerol from whatever source can be detected with a composition comprising 2–4 above. According to a preferred embodiment, the electron acceptor is oxygen and the reagent composition also includes a hydrogen peroxide indicator composition, i.e., reagents which interact with hydrogen peroxide to produce a detectable product. The method can be used for assay of ATP. The method and reagent composition for performing the disclosed assays can be incorporated into a matrix of absorbent material.

67 Claims, 2 Drawing Figures

PROCESS AND COMPOSITION FOR THE QUANTIFICATION OF GLYCEROL ATP AND TRIGLYCERIDES

This is a continuation-in-part of our co-pending application Ser. No. 715,797, filed Aug. 19, 1976 now abandoned.

FIELD OF THE INVENTION

The present invention relates to the analysis of aqueous liquids for triglyceride and/or glycerol content and more specifically to improved methods and compositions for the assay of blood serum triglycerides.

BACKGROUND OF THE INVENTION

The determination of serum triglyceride levels is becoming increasingly important in the diagnosis of several types of hyperlipemia and atherosclerotic heart disease (Kahlke, W. *Med. Wscht.* 91, p. 26 (1966), Kuo, P. T. and Basset, D. R., *Amer. Intern. Med.*, 59, p. 465 (1963). Conventional procedures for serum triglyceride determination involve hydrolyzing the triglyceride to liberate glycerol and treating the glycerol with various reagents to produce a compound that can be quantitated spectrophotometrically. Generally hydrolysis is achieved using a base, however, U.S. Pat. Nos. 3,703,591 to Bucolo et al and 3,759,793 to Stork et al describe enzymatic techniques using a lipase alone ('793) or in combination with a protease ('591) to achieve hydrolysis. Other non-enzymatic saponification techniques are described in German Pat. Nos. 2,229,849 and 2,323,609.

Currently three enzymatic methods are conventionally used for the determination of glycerol from whatever source. These are as follows:

(a) Method of Garland and Randle (Garland, P. B. and Randle, P. J. Nature, 196 p. 987–988 (1962))

glycerol + ATP $\xrightarrow{\text{glycerol kinase}}$ L-α-glycerophosphate + ADP ADP + phosphoenolpyruvate $\xrightarrow{\text{pyruvate kinase}}$ pyruvate + ATP pyruvate + NADH $\xrightarrow{\text{lactate dehydrogenase}}$ lactate + NAD⁺

(b) Weiland's Method (Weiland, O. Biochem Z., 329 p.313 (1957)

glycerol + ATP $\xrightarrow{\text{glycerol kinase}}$ L-α-glycerophosphate + ADP L-α-glycerophosphate + NAD⁺ $\xrightarrow{\text{α-glycerophosphate dehydrogenase}}$ NADH + dihydroxyacetone phosphate + H⁺

(c) Glycerol Dehydrogenase Method (Hagen, J. H. and Hagen, P. B. Can. J. Biochem. and Physiology, 40 p. 1129 (1962))

glycerol + NAD⁺ $\xrightarrow{\text{glycerol dehydrogenase}}$ dihydroxyacetone + NADH + H⁺

Modifications of the method of (a) are also described in German Pat. No. 2,665,556, British Pat. No. 1,322,462 and U.S. Pat. No. 3,759,793. In all cases NADH production or disappearance is measured at 340 nm in a U.V. spectrophotometer. Method (a), utilized in many commercial "kits," is a three enzyme sequence and NADH disappearance is measured. Method (b) involves a two enzyme sequence in which NADH production is measured as is the case with the single enzyme glycerol dehydrogenase reaction (method (c)). The latter two procedures are extremely pH-sensitive and subject to error if strict pH control is not maintained. Also, in all three methods (especially method (a)) stability of not only the diagnostic enzymes but also the cofactor, NADH, is a major concern. Errors in current enzymatic methods are discussed in greater detail in Chen, H. P. and El-Mequid, S. S., *Biochemical Medicine*, 7, p. 460 (1973).

Another method for triglyceride analysis is described in German Pat. No., 2,139,163. The method of this patent involves saponification of the triglycerides, oxidation of the resulting glycerol to formaldehyde and reaction of the formaldehyde with ammonia and a stable, water- and alcohol-soluble, colorless metal complex of acetylacetone to produce a colored compound.

OBJECTS OF THE INVENTION

It is an object of the present invention to provide improved methods and compositions for the quantitation of glycerol and triglycerides, especially serum triglycerides, which methods and compositions are relatively free of any requirement for strict and narrow pH control and major concerns for reagent stability.

SUMMARY OF THE INVENTION

According to the present invention there is provided a novel method for quantification of glycerol (as either a free glycerol or glycerol formed from fatty acid esters of glycerol, e.g., triglycerides) in aqueous liquids comprising the steps of:

(I) contacting in the presence of an electron acceptor;
   (1) a sample of the aqueous liquid; and
   (2) enzymes and other reagents which effect an ordered sequence of reactions, preferably quantitative, wherein fatty acid esters of glycerol, if present, are enzymatically hydrolyzed to glycerol, glycerol whether present in the free form initially or liberated by hydrolysis of the esters is converted to L-α-glycerophosphate which in turn is enzymatically oxidized, producing a detectable change in the presence of triglyceride or generally positive sample; and (II) detecting the occurrence of the detectable change.

According to a preferred embodiment the electron acceptor is oxygen and an indicator composition which produces a detectable product on contact with hydrogen peroxide is included as a reagent. The detectable product is generally a colored material, which, according to a highly preferred embodiment, is quantifiable.

According to yet another preferred embodiment, glycerol is converted to L-α-glycerophosphate using glycerol kinase and the oxidation of L-α-glycerophosphate takes place in the presence of L-α-glycerophosphate oxidase.

A most preferred embodiment utilizes an indicator composition comprising substance having peroxidative activity and a dye precursor; the dye precursor comprising either (1) a compound which forms a dye in the presence of hydrogen peroxide and substance having peroxidative activity or (2) a compound or series of compounds which undergoes no detectable change in the visible range in the presence of hydrogen peroxide and substance having peroxidative activity but which interacts with another compound or series of compounds to produce a quantifiable product proportional to the glycerol or triglyceride content of the sample under analysis.

Chance, B., "Oxidase and Peroxidase Reaction in the Presence of Dihydroxymaleic Acid," Vol. 197, p. 577ff (1952) describes the oxidation of dihydroxymaleic acid in the presence of hydrogen peroxide and peroxidase. Similarly, Yamazaki, Isao, and Yokota, Ken-nosuke, "Oxidation States of Peroxidase," Molecular and Cellular Biochemistry, Vol. 2, No. 1, p. 39–52 (1973) report that ascorbic acid reduces the oxidation state of horseradish peroxidase. Seely, G. R., "Photochemistry of Porphyrins" equates ascorbic acid, and dihydroxymaleic acid with dihydroxyacetone in their ability to reduce zinc tetraphenylporphine.

The common characteristic shared by all of these compounds is the ene-diol structure. Thus, when approaching the aforementioned problem of coupling a reaction which produced dihydroxyacetone phosphate and hydrogen peroxide to a peroxidase linked reaction for quantitating triglycerides, it appeared likely that the dihydroxyacetone phosphate would be such a strong reducing agent that it would be oxidized in the presence of $H_2O_2$ and peroxidase to provide a competing reaction which would interfere with the quantitating reaction of the chromogen with $H_2O_2$ in the presence of peroxidase. Thus, it was entirely surprising that when the α-glycerophosphate oxidase catalyzed decomposition of α-glycerophosphate to dihydroxyacetone phosphate and $H_2O_2$ was linked to the peroxidase catalyzed color-producing reaction that dye was produced stoichiometrically with no apparent interference due to the concomitantly produced dihydroxyacetone phosphate.

DETAILED DESCRIPTION OF THE INVENTION

The method of this invention represents an improvement over prior art methods and compositions in that the instant method and compositions do not rely on the production or disappearance of NADH with its attendant disadvantages which are well recognized and documented in the art.

In the present invention, triglycerides are preferably quantified by the following series of reactions:

TABLE I 1. triglyceride + HOH $\xrightarrow{\text{Lipase}}$ glycerol + fatty acids 2. glycerol + ATP $\xrightarrow{\text{Glycerol Kinase}}$ L-α-glycerophosphate + ADP 3. L-α-glycerophosphate + electron acceptor $\xrightarrow{\text{α-GP oxidase}}$ dihydroxyacetone phosphate + species for analytical determination When oxygen is the electron acceptor $H_2O_2$ is formed as the species for analytical determination in (3) and $H_2O_2$ determination is preferably accomplished according to the following reaction:

4. $H_2O_2 + H_2A$ (red.) $\xrightarrow{\text{Peroxidase}}$ A(ox) + $H_2O$
(detectable species)

Wherein:
$H_2A$ (red.) - dye precursor which is the reduced form of the dye.
A(ox) - dye formed by oxidation of $H_2A$.

In the combined reactions of the preferred composition, formation of the detectable species is proportional to glycerol and/or triglyceride concentration. This system has potential use in many clinical applications, in particular, the determination of serum triglycerides.

The procedure of this invention has many inherent advantages over conventional methods. First, any leuco dye that peroxidase will utilize as an electron donor is potentially useful in the indicator composition; thus one can measure the reaction at one of several wavelengths in the visible region of the spectrum; depending upon dye selection. Secondly, measurements made in the visible region are less subject to interferences than those taken at 340 nm. Third, in addition to dyes, substantially any means for detecting hydrogen peroxide can be used. Fourth, stability of NAD+ or NADH is not a concern since $O_2$ is the cofactor in the α-glycerophosphate oxidase reaction. Fifth, serum components that utilize NAD+ or NADH (for example, lactate plus lactate dehydrogenase) which might interfere with prior art reaction sequences, do not interfere with the instant procedure. Sixth, any means which measures $O_2$ uptake can be used as a detection means when $O_2$ is used as the electron acceptor. Finally, the enzymes used in the proposed sequence are active over a relatively wide pH range; thus stringent pH control is not necessary.

Although the discussion hereinafter will center primarily around solutions and solution methods for quantifying glycerol and triglycerides, it should be readily apparent to the skilled artisan that all of the reagents may be provided in dry or lyophilized form and reconstituted with water immediately prior to use. Compositions of this type are clearly contemplated hereby.

Hydrolysis:

In its most sophisticated embodiment the method of the present invention is utilized to assay aqueous liquids, for example blood serum, for triglyceride content. According to this embodiment triglycerides are saponified to free glycerol by means of any of the well known techniques described in the art. Enzymatic techniques are preferred for obvious reasons. These generally involve treatment of the serum sample with a lipase of one sort or another, either in combination with an effector such as a protease or a surfactant or alone depending upon the nature of the triglyceride. Detailed discussions of such techniques and useful compositions for their performance are contained in U.S. Pat. No. 3,703,591 to Bucolo et al issued Nov. 21, 1972 and U.S. Pat. No. 3,759,793 to Stork et al issued September 18, 1973. Bucolo et al uses a lipase preferably from *Rhizopus arrhizus* (var. delemar) and similar materials in combination with a protease to achieve saponification of serum triglycerides while Stork et al discloses the use of lipase from *Rhizopus arrhizus* alone to achieve saponification.

A further method for the hydrolysis of serum triglycerides is described in concurrently filed and commonly assigned U.S. Patent Application Ser. No. 715,798 entitled "Hydrolysis of Protein-Bound Triglycerides." This technique involves the hydrolysis of serum triglycerides using a compatible mixture of a lipase which normally, of itself, is not capable of hydrolyzing protein associated triglycerides as found in serum and, as an effector, a compatible surfactant. A compatible surfactant is one which stimulates triglyceride hydrolysis by the lipase as described in the test below. Thus, such a surfactant will not inhibit the activity of the lipase, but actually enhance it. The lipase is preferably from *Candida cylindracea* (*Candida rugosa*).

Useful lipases for triglyceride hydrolysis according to any of the foregoing techniques may be of plant or animal origin, but we prefer and find best, particularly for use in the compositions described in aforementioned Ser. No. 715,798 microbial lipases, such as the lipase from *Candida cylindracea,* when the lipase is used in combination with a surfactant as described below. Lipases from *Chromobacterium viscosum,* variant paralipolyticum crude or purified, the lipase from *Rhizopus arrhizus* (variant delemar), purified, for example, as noted in Fukumoto et al, *J. Gen. Appli. Microbiol,* 10, 257–265 (1964) and lipase preparations having similar activity are also useful.

Other useful lipases and methods for their preparation are described in the following U.S. Pat. Nos.:

2,888,385 to Grandel issued May 26, 1959;
3,168,448 to Melcer et al issued Feb. 2, 1965;
3,189,529 to Yamada et al issued June 15, 1969;
3,262,863 to Fukumoto et al issued July 26, 1966; and
3,513,073 to Mauvernay et al issued May 19, 1970.

To the extent the descriptions contained in the foregoing materials are pertinent and not detailed herein, they are incorporated herein by reference. Since the lipases are readily available in lyophilized form, they are easily incorporated into either dry mixtures for reconstitution with water or provided as stable solutions of reagent which can be combined with other such solutions to provide reaction mixtures for contact with samples for analysis.

Specifically preferred commercial lipases include wheat germ lipase supplied by Miles Laboratories of Elkhart, Ind., Lipase 3000 supplied by Wilson Laboratories, Steapsin supplied by Sigma Chemical Company (both of the latter are pancreatic enzymes), and Lipase M (from *Candida cylindracea* (*Candida rugosa*)) supplied by Enzyme Development Company.

Nonionic and anionic surfactants have been found useful in combination with lipase preparations which of themselves are incapable of hydrolyzing serum triglycerides. Most preferred from among such materials are the octyl and nonyl phenoxy polyethoxy ethanols such as those commercially available from Rohm and Haas Company under the Triton trademark. Best results are obtained with such surfactants when the HLB number (hydrophile-lipophile: balance) is below about 15 and the number of polyoxyethylene units in the polyoxyethylene chain is less than about 20.

Compatible compositions of lipase and surfactant are readily defined by the following test:

The surfactant of the composition under evaluation is added to unbuffered reconstituted serum (specifically Validate, a serum standard available from General Diagnostics Division of Warner Lambert Company, Morris Plains, N.J.) at varying concentrations of between about 0 and 10% by weight and the solution incubated for about 5 minutes at 37° C. At this time, a sample of the proposed lipase preparation is added and incubation continued for a period of about 20 minutes. Aliquots (~0.2 ml) of this solution are then diluted to 1.6 ml with water (containing 1.3 mM $CaCl_2$ to aid precipitate formation), placed in a boiling water bath for ten minutes and centrifuged to clarify (4° C., 37,000 Xg, 10 minutes). Glycerol in a 0.4 ml aliquot of the clear supernatant is quantitated in a total volume of 1.2 ml by the method described by Garland, P. B. and Randle, P. J., Nature, 196, 987–988 (1962). Any composition which effects release of at least about 50% of the theoretical concentration of available glycerol is considered useful and within the scope of the present invention. When performing the foregoing test it is most desirable to run a blank which contains all of the components of the mixture but the lipase preparation so that any reaction which may be due to free glycerol or other components of the serum can be subtracted. The preferred compositions accomplish at least 75% hydrolysis of the available triglyceride to glycerol in less than 10 minutes and most preferred are those which achieve substantially complete hydrolysis of the available triglyceride to glycerol, i.e., above about 90%, in less than about 10 minutes. Examples of such preferred compositions are shown in Table I below.

When, for one reason or another, the protease-lipase combination of the prior art is used for hydrolysis, proteases in general may be used. These include by way of example, chymotrypsin, *Streptomyces griseus* protease (commercially available under the registered trademark "Pronase"), proteases from *Aspergillus oryzae* and *Bacillus subtilis,* elastase, papain, and bromelain. Mixtures of such enzymes may, of course, be employed.

The useful concentrations of lipase and other effectors such as surfactants, protease, etc. will vary broadly depending upon the time limitations imposed on the assay, etc. and these are readily determined by the skilled artisan. Typical nonlimiting examples of useful concentrations are described in the examples below.

Saponification of triglycerides can also be achieved using any of the well known prior art "non-enzymatic" techniques for obtaining the free glycerol prior to assay according to the present method including treatment with a strong base. Caution must be exercised, however, to insure that the glycerol is delivered to the enzymatic glycerol assay composition in a medium which does not contain materials which would inhibit the enzymes of the glycerol assay system or otherwise interfere with the reactions necessary to achieve an accurate glycerol determination.

Glycerol Assay

Once triglyceride hydrolysis has been achieved by whatever means, the novel enzymatic glycerol assay of the present invention can be implemented.

As shown in the reaction above, the first enzyme used in the glycerol assay is glycerol kinase which catalyzes the conversion of glycerol to L-α-glycerophosphate in the presence of adenosine triphosphate (ATP). Generally, any glycerol kinase is useful in the successful practice of the present invention although those obtained from *E. coli* and *Candida mycoderma* are preferred. Other glycerol kinase enzymes are well known in the art. A complete discussion of such materials and further references to their preparation and reactivity may be found in T. E. Barman, *Enzyme Handbook*, I, Springer-Verlag, N.Y. (1969) pgs. 401–402. Glycerol kinase from Worthington Biochemical Company provides a satisfactory commercial source of the enzyme.

The next step in the reaction sequence involves the oxidation of L-α-glycerophosphate in the presence of L-α-glycerophosphate oxidase and an electron acceptor to produce a detectable change. The detectable change is preferably a color change or color formation which, in the preferred case, is quantitatively related to the glycerol contained in the liquid sample. Other detectable changes such as oxygen consumption may also be monitored to detect the analytical result.

Any electron acceptor which will permit oxidation of the α-glycerophosphate by the oxidase enzyme with the concomitant production of a detectable change is a suitable candidate for use in this reaction. Particularly preferred as electron acceptors are materials which provide, directly or indirectly, a radiometrically detectable, preferably colored product. The utility of any particular electron acceptor can only be determined by trial and error with potentially useful electron acceptors.

A highly preferred electron acceptor is oxygen which will oxidize the L-α-glycerophosphate in the presence of the oxidase to dihydroxyacetone phosphate and hydrogen peroxide. Methods for determining hydrogen peroxide and measuring the consumption of oxygen in reactions of this type are, of course, well known. An alternative preferred embodiment uses as electron acceptor material colored or uncolored which undergoes a change in or the production of color directly upon reduction in the presence of the enzyme and the substrate. As described above, such materials can only be selected by testing in a specific use environment. Such an environment is described in Example 5 below. Using this method certain indolphenols, potassium ferricyanide and certain tetrazolium salts have been found to be useful electron acceptors. Specifically, 2,6-dichlorophenolindolphenol alone or in combination with phenazine methosulfate and 2-(*p*-indophenyl)-3-(*p*-nitrophenyl)-5-phenyl-2H-tetrazolium chloride either alone or in combination with phenazine methosulfate have been found useful as electron acceptors in this reaction.

The detectable change may also be determined using potentiometric techniques, for example, by measuring oxygen consumption using an oxygen electrode.

L-α-glycerophosphate oxidase is a microbial enzyme which can be derived from a variety of sources. The properties of enzyme from certain sources are more desirable than those from others as will be elaborated below. Generally, the enzyme may be obtained from Streptococcaceae, Lactobacillaceae and Pediococcus. The enzyme from cultures of *Streptococcus faecalis*, specific strains of which are obtainable from the American Type Culture Collection, are specifically preferred. Particularly useful and preferred enzymes are obtained from strains ATCC 11700, ATCC 19634 and ATCC 12755 identified on the basis of their deposit in that collection. As will be described and demonstrated by example below, the enzyme from ATCC 12755 demonstrates activity over a somewhat broader pH range than enzymes derived from the other two strains and for this reason is most preferred.

The following reference describes both the enzyme and useful techniques for its preparation and extraction, Koditschek, L. K. and Umbreit, W. W., "α-Glycerophosphate Oxidase in *Streptococcus faecium*, F 24," Journal of Bacteriology, Vol. 98, No. 3, p. 1063–1068 (1969). Enzymes prepared according to the methods described in this publication are useful in the successful practice of the invention. When any enzyme preparation of unknown total composition is used, care should be exercised to extract any contaminants which may interfere with assay results. For example, certain preparations of L-α-glycerophosphate oxidase, derived as described below, contained sufficiently high concentrations of impurities specifically lactate oxidase that the crude preparation had to be purified using conventional fractionation and column separation techniques before assays of blood serum triglycerides free from unwanted interferences could be achieved.

It should be noted that although Koditschek et al used the production of $H_2O_2$ to characterize the α-glycerophosphate oxidase producing microorganism, they neither attempted nor suggested the utility of the enzyme in an assay or quantification system, but merely noted that the enzyme catalyzed a reaction which produced hydrogen peroxide.

Quantification of glycerol in aqueous solutions containing glycerol and/or triglycerides, for example, blood serum, is preferably achieved using an indicator composition which detects the level of hydrogen peroxide produced in the oxidation of L-α-glycerophosphate in the presence of oxygen. Indicator compositions for the detection of enzymatically generated hydrogen peroxide are well known in the art, particularly as indicator compositions in the enzymatic detection of glucose and uric acid. U.S. Pat. Nos. 3,092,465 and 2,981,606 among many others describe such useful indicator compositions.

The hydrogen peroxide indicator composition generally comprises a substance having peroxidative activity, preferably peroxidase, and an indicator material (i.e., a chromogen) which undergoes a color formation or change in the presence of hydrogen peroxide and peroxidase. Alternatively, the indicator material may be one or more substances which undergo no substantial color change upon oxidation in the presence of $H_2O_2$ and peroxidase, but which in their oxidized form react with a color-forming or -changing substance (e.g., a coupler) to give visible evidence of chemical reaction. U.S. Pat. No. 2,981,606 in particular provides a detailed description of such color indicator compositions. The latter color forming composition, i.e., one which produces color by virtue of an intermediate or color coupling reaction, is preferred in the practice of the present invention.

A peroxidase is an enzyme which will catalyze a reaction wherein hydrogen peroxide oxidizes another substance. The peroxidases are generally conjugated proteins containing iron porphyrin. Peroxidase occurs in horseradish, potatoes, figtree sap and turnips (plant peroxidase); in milk (lacto peroxidase); and in white blood corpuscles (verdo peroxidase); also it occurs in microorganisms. Certain synthetic peroxidases, such as disclosed by Theorell and Maehly in Acta Chem. Scand., Vol. 4, pages 422–434 (1950), are also satisfactory. Less satisfactory are such substances as hemin, methemoglobin, oxyhemoglobin, hemoglobin, hemochromogen, alkaline hematin, hemin derivatives, and certain other compounds which demonstrate peroxidative or peroxidase-like activity, namely, the ability to catalyze the oxidation of another substance by means of hydrogen peroxide and other peroxides.

Other substances which are not enzymes but which possess peroxidase-like activity are: iron sulfocyanate, iron tannate, ferrous ferrocyanide, chromic salts (such as potassium chromic sulfate) absorbed in silica gel, etc. These substances are not as satisfactory as peroxidase per se but are similarly useful.

Color-forming substrates (i.e., chromogens) of peroxidase and peroxidase-like substances which produce a color formation in the presence of hydrogen peroxide and peroxidase which may be employed in indicator compositions useful in the present invention include the following substances, with a coupler where necessary:

(1) Monoamines, such as aniline and its derivatives, ortho-toluidine, para-toluidine, etc.;

(2) Diamines, such as ortho-phenylenediamine, N,N'-dimethyl-para-phenylenediamine, N,N'-diethyl phenylenediamine, benzidine (which produces a blue or brown color), dianisidine (turns green or brown), etc.;

(3) Phenols, such as phenol per se (producing a yellow color), thymol, ortho-, meta- and para-cresols (producing a green-yellow color, a pink color and a milky suspension, respectively), alpha-naphthol (producing a magenta color), beta-naphthol (producing a white precipitate), etc.;

(4) Polyphenols, such as catechol, guaiacol (which forms an orange color), orcinol, pyrogallol (producing a reddish or yellow color), p,p-dihydroxydiphenyl and phloroglucinol;

(5) Aromatic acids, such as salicyclic, pyrocatechuic and gallic acids;

(6) Leuco dyes, such as leucomalachite green (to produce malachite green) and leucophenolphthalein (desirably employed in an alkaline medium);

(7) Colored dyes, such as 2,6-dichlorophenolindophenol;

(8) Various biological substances, such as epinephrine, the flavones, tyrosine, dihydroxyphenylalanine (producing an orange-reddish color) and tryptophan;

(9) Other substances, such as gum guaiac, guaiaconic acid, potassium, sodium, and other water soluble iodides; and bilirubin (producing a greenish color); and (10) Such particular dyes as 2,2'-azine-di(3-ethylbenzothiazoline-(6)-sulfonic acid) and 3,3'-diaminobenzidine.

Other materials or compositions that contain material oxidizable in the presence of peroxidase and can provide a radiometrically detectable species include certain dye-providing compositions. In one aspect dye-providing compositions can include a compound that, when oxidized by peroxidase, can couple with itself or with its reduced form to provide a dye. Such autocoupling compounds include a variety of hydroxylated compounds such as orthoaminophenols, 4-alkoxynaphthols, 4-amino-5-pyrazolones, cresols, pyragallol, guaiacol, orcinol, catechol phloroglycinol, p,p-dihydroxydiphenyl, gallic acid, pyrocatechuic acid, salicyclic acid, etc. Compounds of this type are well known and described in the literature, such as in *The Theory of the Photographic Process*, Mees and James Ed, (1966), especially at Chapter 17. In another aspect, the detectable species can be provided by peroxidase induced oxidation of a leuco dye to provide the corresponding dyestuff form. Representative leuco dyes include such compounds as leucomalachite green and leucophenolphthalein. Other leuco dyes, termed oxichromic compounds, are described in U.S. Pat. No. 3,880,658 and it is further described that such compounds can be diffusible with appropriate substituent groups thereon. The non-stabilized oxichromic compounds described in U.S. Pat. No. 3,880,658 are considered preferable in the practice of this invention. In yet another aspect, the detectable species can be provided by dye-providing compositions that include a peroxidase-oxidizable compound capable of undergoing oxidative condensation with couplers such as those containing phenolic groups or activated methylene groups, together with such a coupler. Representative such oxidizable compounds include such compounds as benzidene and its homologs, p-phenylenediamines, p-aminophenols, 4-aminoantipyrine, etc. A wide range of such couplers, including a number of autocoupling compounds, is described in the literature, such as in Mees and James (supra) and in Kosar, *Light-Sensitive Systems*, 1965, pages 215–249.

The color indicator composition of the present invention preferably comprises 4-methoxy-1-naphthol which undergoes self coupling in its oxidized state or a combination of 1,7-dihydroxynaphthalene and 4-aminoantipyrine (HCl). In the latter composition the oxidized pyrine compound couples with the dihydroxynaphthalene. The concentrations of the components of the various color indicator compositions useful in the elements described herein are dependent to a large extent upon the concentration of glycerol in the sample, the sophistication of the detection apparatus, the dye produced, etc., and are readily determinable by the skilled artisan. Typical values are shown in the examples below.

Of course, other means for detecting hydrogen peroxide may also be used in the successful practice of the present invention. For example, enzymes and other reagents as described herein can be incorporated into membranes of oxygen sensitive polarographic electrodes as described in Rawls, Rebecca L., "Electrodes Hold Promise in Biomedical Uses," Chemical and Engineering News, Jan. 5, 1976, p. 19.

As a further alternative, instead of measuring the hydrogen peroxide produced, it is also possible to measure oxygen uptake using an oxygen sensitive electrode and thereby determine the quantity of glycerol produced in above-described reaction (1) of Table I which would result in the consumption of that quantity of oxygen in reaction (3) in Table I.

The concentration of the other components of the novel assay compositions described herein may also vary broadly depending upon the solution under assay (i.e. blood serum, diluted or undiluted, or other complex aqueous solution of glycerol and/or triglycerides). Table II below provides a ready reference for the generally useful and preferred concentration ranges of the various components of the novel assay compositions described herein.

TABLE II

| Enzyme | Generally useful range U/ml | Preferred level U/ml |
| --- | --- | --- |
| Lipase (when used) | 20–160 | 80 |
| Glycerol kinase | .05–1 | 0.2 |
| Glycerophosphate oxidase | 1–10 | 4 |
| Protease (when used) | 300–2400 | 1200.0 |
| Peroxidase | 0.2–1.4 | 0.7 |
| | g/ml | g/ml |
| Surfactant (when used) | .01–.05 | .02 |

Of course useful results may be obtained outside of these ranges; however, these have generally been found useful and preferred as indicated.

In the foregoing Table II, one international unit of enzyme is defined as that quantity of enzyme which results in the conversion of one micromole of substrate in one minute at 37° C. and pH 7.

As is well recognized in the art, each of the enzymes possesses a pH-activity profile, i.e., the activity of the enzyme varies with pH. These data are described in detail for α-glycerophosphate oxidase in the Examples. As demonstrated by that data, the pH activity profile of L-α-glycerophosphate oxidase peaks at between about pH 5 and 8.5. The pH range over which each of the enzymes in the novel reaction sequence is most active is shown in Table III.

TABLE III

| | pH-value |
| --- | --- |
| Lipase | 5–9 |
| Glycerol kinase | 7–9 |
| L-α-Glycerophosphate oxidase | 6.3–8.0 |
| Peroxidase | 6–8 |

From the foregoing table, it is readily apparent that it is most desirable to buffer the assay compositions described herein at a pH of between about 6.0 and about 8.0 and most preferably between about 7.0 and about 8.0. Techniques for achieving this type of buffering are well known in the art and involve dissolving, dispersing, or otherwise distributing, suitable concentrations of buffer materials in the reagent composition or, alternatively, providing them in dry form when a reconstitutable mixture is provided. Suitable buffers for buffering to the aforementioned pH levels are described in detail by Good in *Biochemistry* 5, 467 (1966). Particularly preferred buffers are the phosphates such as potassium phosphate.

The concentration of detectable species produced can, of course, be detected using any of the well known methods. For example, by comparison to a standard color chart, spectrophotometrically, etc.

The following enzyme preparation techniques and standardized procedures and compositions were used in the examples which follow.

Standard Solutions: Exact concentrations of glycerol standard solutions were determined by the method of Garland and Randle (*Nature*, 196, 987–988 (1962)). Hydrogen peroxide solutions were standardized by measuring the $A_{240}$ (optical absorbance at 240 nm) and using $E_{240} = 43.6$ for pertinent calculations. Serum samples were analyzed for triglyceride concentration by the semi-automated fluorometric method of Kessler and Lederer (*Fluorometric Measurement of Triglycerides, Automation in Analytical Chemistry*, Technican Symposia, L. T. Sheggs, Jr., Ed., Medical Inc., N.Y., N.Y. 341 (1966)).

Glycerol and Triglyceride Quantitation by the α-GP Oxidase Method: Incubation mixtures for glycerol detection contained in a total volume of 1.0 ml: 200 μmoles potassium phosphate buffer, pH 8.0, 4.2 purpurogallin units horseradish peroxidase. 2.5 μmoles $MgSO_4$, 2.4 μmoles ATP, 10 mg Triton X-100, 96 μg 4-aminoantipyrene hydrochloride, 32 μg 1,7-dihydroxynaphthalene (added as an 0.8% solution in ethanol), and 4 units of α-GP oxidase (excess glycerol kinase was present in the α-GP oxidase preparation). For triglyceride quantitation, incubation mixtures contained 10 mg (8 units/mg) lipase from *Candida rugosa* in addition to the above components. All components were equilibrated at 37° C. for five minutes and $A_{490}$ (initial) was determined. Reactions were initiated by addition of either a glycerol standard (5–100 nmoles) or serum (20 μl) and allowed to proceed for 20 to 30 minutes. The $A_{490}$ (final) was then measured. Variations of this standard system are indicated where necessary.

Calculation of Triglyceride Concentrations: Triglyceride glycerol concentrations of unknown samples were determined in the following way: The $\Delta A_{490}$ ($A_{490}$ (final) minus $A_{490}$ (initial)) for samples incubated in the presence of the standard glycerol detection system was subtracted from the $\Delta A_{490}$ of the same samples incubated in the presence of Lipase M and the standard glycerol detection system. Triglyceride concentrations were determined from this Lipase M dependent change in absorbance by use of a calibration with either glycerol or pre-analyzed serum samples as standards.

Growth of *S. faecalis*

*S. faecalis* (species designated in Table IV below) was maintained on slants containing 0.1% glucose, 1% tryptone, 1% yeast extract, 0.65% $K_2HPO_4$ and 1.5% agar. Water suspensions of the slant colonies (0.2 ml of 1.0 ml suspension per flask) were used to inoculate flasks filled with 25 ml of media each. These were shaken at 120 rpm (2 inch throw) in a New Brunswick Psycrotherm Incubator Shaker at 30° C. for 22 hours.

Preparation of Cell-Free Extracts

The cells from 100 ml of media were harvested by centrifugation (4° C., 10,000 X g, 10 min), washed with 40 ml of cold 0.05 M potassium phosphate buffer, pH 7.0, centrifuged again, and suspended in 10 ml of buffer. Cells then were disrupted by sonication (Branson J-17A sonifier operating at a setting of 40) in a Rosett cooling cell for 7 minutes; the temperature was maintained below 8° C. The supernatant from a centrifugation at 10,000 × g for 10 minutes was used as enzyme source. In all cases the amount of soluble protein had reached a maximum during the indicated sonication period. Using bovine serum albumin as standard, protein concentration was determined by the method of Lowry et al (Lowry, D. H., Roseborough, N. S., Farr, A. L. and Randall, R. J., *J. Biol. Chem.* 193, 265 (1951)).

Isolation of α-Glycerophosphate Oxidases from *Streptococcus faecalis*

The results in Table IV compare α-glycerophosphate oxidases isolated from three strains of *Streptococcus faecalis*. In each case the organism was cultured aerobically at 30° C. for 22 hours in a glucose medium; cells were collected by centrifugation and then disrupted by sonication. Routinely the supernatant from a 10,000 × g centrifugation was used as enzyme source (crude extract). However, the oxidases remained in solution even after centrifugation at 100,000 × g for 1 hour. In all cases the rate of decrease in dissolved oxygen was proportional to the amount of crude extract and was absolutely dependent on both D,L-α-glycerophosphate and the extract. As can be seen, all three strains displayed oxygen-linked activity. The enzyme from strain ATCC 11700 reportedly has a pH optimum of 5.8 and the oxidase from strain ATCC 19634 displays a maximum at pH 7.0. This trend is also seen in Table IV. By analogy the activity from strain 12755 was similar to the one from strain ATCC 19634.

TABLE IV

Isolation of α-Glycerophosphate Oxidases
from Three Strains of
*Streptococcus faecalis*

Reactions were carried out at 21° in 0.05 M
potassium phosphate buffer at the pH indicated
with 0.13 M DL-α-glycerophosphate as substrate.

| S. faecalis culture | pH of Incubation Mixture | Decrease in % Dissolved $O_2$ Δ %/min/mg |
|---|---|---|
| ATCC 11700 | 6.0 | 4.52 |
|  | 7.3 | 1.49 |
| ATCC 19634 | 6.1 | 3.94 |
|  | 7.5 | 6.90 |
| ATCC 12755 | 5.9 | 4.93 |
|  | 6.8 | 7.10 |

Oxygen Electrode Assay of α-Glycerophosphate Oxidase

L-α-Glycerophosphate oxidase was assayed by measuring the decrease in dissolved oxygen with a New Brunswick D.O. Analyzer. The oxygen electrode was calibrated against both $N_2$ and air saturated water with constant agitation provided by a magnetic stirrer. Incubation mixtures containing buffer and D,L-α-glycerophosphate in a total volume of 7.5 ml were allowed to equilibrate at 21° C. Then reaction was initiated by enzyme addition and the rate of decrease in dissolved oxygen was calculated from the linear portion of the curve. Exact conditions and concentrations for each experiment are given where appropriate.

Spectrophotometric Assay of α-Glycerophosphate Oxidase

α-GP oxidase was assayed with a reagent containing in a total volume of 1.0 ml: 100 μmoles potassium phosphate buffer, pH 7.0, 66 μg o-dianisidine, 25 μg horseradish peroxide (4.6 purpurogallin units) and 200 μmoles D,L-α-glycerophosphate (at pH 7.0). The reagent was equilibrated at 37°, and the reaction was initiated by the addition of an aliquot of enzyme. Activity was calculated from the initial linear slope of the reaction trace at 430 nm, with $\epsilon = 1.08 \times 10^4$.

Properties of the α-Glycerophosphate Oxidase in Crude Extracts

Figure 1:
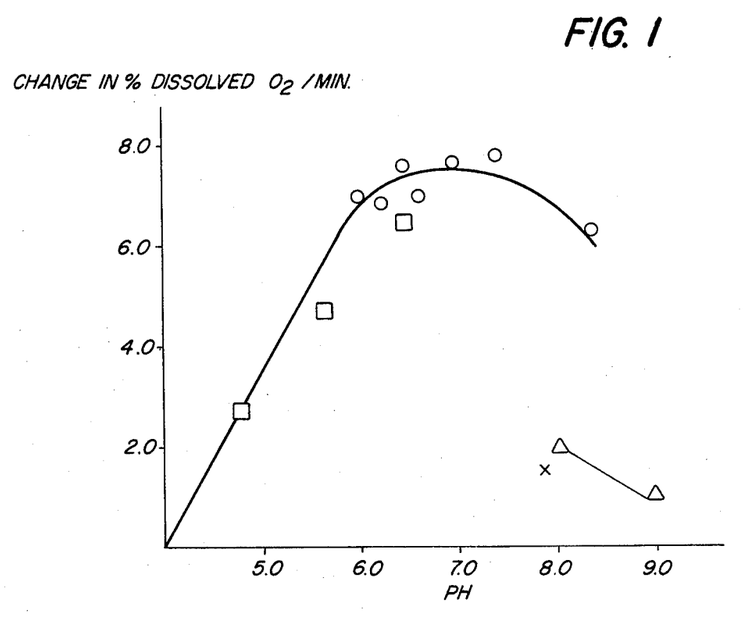
FIG. 1 is a graph showing the pH profile of a preferred α-glycerophosphate oxidase.

A detailed pH-activity profile of the α-glycerophosphate oxidase from strain 12755 is shown in FIG. 1. Optimum activity was observed over the broad pH range of 6.3 to 7.5; below pH 6.0 and above pH 8.0 activity decreased rapidly. Also shown in FIG. 1 is the apparent inhibition of the enzyme by either tris-HCl (Δ-Δ) or glycine-KOH (X) buffers. At pH 7.7 the activity in 0.1 M potassium phosphate buffer was 4-times that observed in 0.1 M glycine-KOH. However, when an incubation was carried out in the presence of both 0.1 M glycine-KOH and 0.07 M potassium phosphate buffer, pH 7.7, 82% of the original activity (in presence of 0.1 M potassium phosphate buffer) was restored. This suggests that tris-HCl and glycine-KOH were not inhibitors, but rather that potassium phosphate buffer activated the enzyme. Sodium acetate buffer also must stimulate the enzyme (FIG. 1), since at pH 6.5 activity in sodium acetate buffer was at least 90% that observed in potassium phosphate buffer.

L-α-Glycerophosphate Oxidase Purification

Preliminary investigations of the α-glycerophosphate oxidase-glycerol detection system indicated that the crude α-glycerophosphate (α-GP) oxidase preparation contained impurities. Some of these impurities apparently prevented the use of the crude enzyme in serum studies since substrates for these enzymes were apparently present in the serum at concentrations comparable to normal triglyceride levels. Certain of these impurities also acted on substrates present in serum to produce hydrogen peroxide which, of course, interfered with the preferred detection technique. The results of purification using protein fractionation techniques are shown in Table V.

TABLE V

PURIFICATION OF α-GLYCEROPHOSPHATE
OXIDASE FROM *S. FAECALIS* ATCC 12755

| PROCEDURE | TOTAL UNITS* α-GP OX | Total protein, mg | Units α-GP OX mg protein | Purification | Yield |
|---|---|---|---|---|---|
| Crude cell-free extract | 6300 | 9850 | 0.64 | 1 | 100 |
| Protamine . $SO_4$ fractionation (0.05%) | 6280 | 9540 | 0.66 | 1.03 | 100 |
| Ammonium . $SO_4$ fractionation (50–80%) | 5590 | 4700 | 1.2 | 1.9 | 89 |
| DEAE-cellulose fractionation | 3600 | 1007 | 3.6 | 5.6 | 57 |
| Dialysis and Concentration | 4250 | 1007 | 4.22 | 6.6 | 68 |

*1 unit = amount of enzyme required to convert 1 μmole substrate to 1 μmole product in 1 minute at 37°.

Stability of α-Glycerophosphate Oxidase

The enzyme solution was completely stable for at least four months when stored frozen at −20° C. Repeated freezing and thawing did not denature the enzyme. Also the enzyme was not inhibited by Triton X-100 even at surfactant concentrations as high as 2%.

The following examples serve to illustrate particular embodiments of the present invention.

EXAMPLE 1: CALIBRATION CURVE FOR GLYCEROL AND HYDROGEN PEROXIDE

Figure 2:
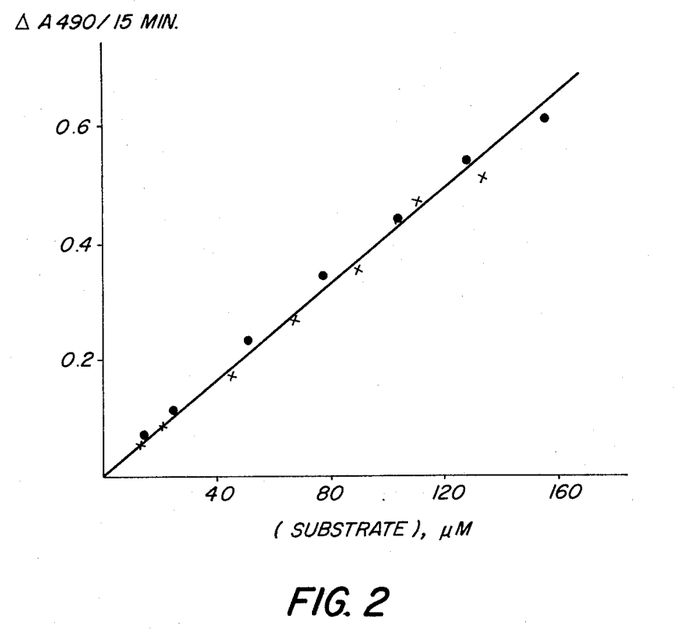
FIG. 2 is a calibration curve for glycerol determinations made using hydrogen peroxide to produce the detectable change in the methods and compositions of the present invention.

A glycerol response curve is shown in FIG. 2. Mixtures were prepared as described above under Glycerol and Triglyceride Quantitation by the α-GP Oxidase Method. Reactions were initiated by substrate addition and were essentially complete in 15 minutes at 37° C. A good relationship between glycerol concentrations (.) and dye formation (x) was observed for coupled reactions 2, 3 and B 4. For comparison, calibration data for hydrogen peroxide are also shown in FIG. 2. Both sets of data were used to construct a single curve indicating essentially complete production of hydrogen peroxide from a stoichiometric amount of glycerol.

EXAMPLE 2: QUANTITATIVE DETERMINATION OF A TRIGLYCERIDE SUBSTRATE

A triglyceride emulsion was prepared by sonicating olive oil (3.6 µmoles/ml) in 0.4% Triton X-100 (octyl phenoxy polyethoxyethanol—available from Rohm and Haas Company) in an ice bath for 10 minutes.

Quantitative determination of the triglyceride substrate by coupling reactions 1, 2, 3 and 4 were compared to quantitative determination by the method of Garland and Randle. Sufficient lipase from *Candida rugosa* was added to catalyze rapid (less than one minute) and complete hydrolysis of the triglyceride. Triglyceride glycerol was determined by comparing the $\Delta A_{430}$ after a 30 minute incubation to the glycerol concentration response curve similar to FIG. 2. The results, shown in Table VI demonstrate good agreement between the two methods. Triglyceride values determined with the α-glycerophosphate oxidase method were slightly higher in all cases but the difference was greater than 10% only in sample 2.

TABLE VI

| | Triglyceride Concentration | |
|---|---|---|
| Sample | Garland and Randle | α-Glycerophosphate Oxidase Method |
| 1 | 18.4 | 19.0 |
| 2 | 36.8 | 42.0 |
| 3 | 73.6 | 78.0 |
| 4 | 110.0 | 114.0 |

EXAMPLE 3: QUANTITATIVE DETERMINATION OF SERUM TRIGLYCERIDES BY THE α-GLYCEROPHOSPHATE OXIDASE METHOD

By means of the preferred buffer system of 0.2 M potassium phosphate buffer at pH 8.0, ten serum samples were assayed for triglyceride glycerol in concentrations ranging from 0.50 to 6.50 mM.

Control mixtures contained only the standard components for glycerol detection; sample mixtures contained lipase from *Candida rugosa* plus the standard components for glycerol detection. All mixtures were equilibrated at 37° C. for 5 minutes and the initial $A_{490}$ was determined. Reactions were initiated by addition of 20 µl of each serum sample and after 20 minutes incubation, the final $A_{490}$ was measured. Triglyceride glycerol concentrations were determined from an aqueous glycerol calibration curve such as in FIG. 2 after the $\Delta A_{490}$ of the controls were subtracted from the $\Delta A_{490}$ of the samples. Results of comparison to the reference method of Kessler and Lederer are shown in Table VII. Good agreement was observed between the two methods.

TABLE VII

Comparison of Serum Triglyceride Quantitative Determination by the α-Glycerophosphate Oxidase System to a Semi-Automated Chemical Method

| | Triglyceride Concentration | | | |
|---|---|---|---|---|
| | Reference Method | | α- Glycerophosphate Oxidase Method | |
| Sample | mM | mg/dl | mM | mg/dl |
| 1 | 6.59 | 560.15 | 6.48 | 550.80 |
| 2 | 4.82 | 409.70 | 4.90 | 416.50 |
| 3 | 3.76 | 319.60 | 3.97 | 337.45 |
| 4 | 3.30 | 280.50 | 3.70 | 314.50 |
| 5 | 2.00 | 170.00 | 1.90 | 161.50 |
| 6 | 1.71 | 145.35 | 1.10 | 93.50 |
| 7 | 1.06 | 90.10 | 0.50 | 42.50 |
| 8 | 0.59 | 50.15 | 0.63 | 53.55 |
| 9 | 1.25 | 106.25 | 1.35 | 114.75 |
| 10 | 1.00 | 85.00 | 0.95 | 80.75 |

EXAMPLE 4

The precision of the method described herein was tested by repetitive assay of two different pooled serum samples; one contained a normal and one contained a high triglyceride level. The results are shown in Table VIII. Coefficients of variation of 5.1% and 2.6% were calculated for the normal and abnormal sera respectively.

TABLE VIII

Reproducibility of the α-GP Oxidase System for Triglyceride Quantitative Determination

| Triglyceride Concentration mM | |
|---|---|
| Normal Serum Level | High Serum Level |
| 1.60 | 4.90 |
| 1.66 | 4.82 |
| 1.61 | 4.80 |
| 1.42 | 5.25 |
| 1.62 | 4.76 |
| 1.55 | 5.00 |
| 1.54 | 4.78 |
| 1.70 | 4.92 |
| 1.66 | 4.96 |
| 1.54 | 4.83 |
| | 4.91 |
| | 4.79 |
| | 4.90 |
| | 4.80 |
| mean 1.59 | 4.89 |
| S.D. ± 0.081 | 0.13 |
| COV 5.10 | 2.60 |

EXAMPLE 5: ALTERNATE ELECTRON ACCEPTORS

To illustrate electron acceptors other than oxygen, reaction mixtures containing the following ingredients were prepared:

0.1 M potassium phosphate buffer to pH 7;
0.2 M D,L-α-glycerophosphate;
electron acceptor as and at the level specified in Table IX.

In each instance the mixture was equilibrated at 37° C. and the reaction was initiated by enzyme addition. The activity of the enzyme was calculated as described hereinabove using $E_{600} = 16 \times 10^3$ for 2,6-dichloroindophenol, $E_{400} = 1 \times 10^3$ for $K_3Fe(CN)_6$ and $E_{505} = 18.5 \times 10^3$ for 2-(p-indophenyl)-3-(p-nitrophenyl)-5-phenyl-2 M-tetrazolium chloride (INT).

The results are shown in Table IX.

TABLE IX

Alternate Electron Acceptors for αGP Oxidase Reaction

| Electron Acceptor | μmoles αGP oxidized/ min/mg | Relative Rate≠ |
|---|---|---|
| Oxygen | 80 | 1 |
| 2,6-Dichlorophenolindolphenyl (70 μm) | 4 | 0.05 |
| 2,6-Dichlorophenolindolphenol (70 μm) Phenazine Methosulfate (60 μm) | 70 | 0.88 |
| $K_3Fe(CN)_6$ (1 mM) | 21 | 0.26 |
| $K_3Fe(CN)_6$ (1 mM) Phenazine Methosulfate (60 μm) | 35 | 0.44 |
| INT* (0.16 mM) | 0.8 | 0.01 |
| INT (0.16 mM) Phenazine Methosulfate (60 μm) | 12 | 0.15 |

≠Rate compared to that with oxygen as electron acceptor
*INT = 2-(p-Indophenyl)-3-(p-nitrophenyl)-5-phenyl-2H-tetrazolium chloride The method described herein can of course be used to quantify any one of the various reagents and enzymes used in the total reagent system. For example, ATP can be determined with a composition which includes all of the reagents except ATP which would be introduced by the sample for assay. Similarly, glycerol kinase, lipase and α-glycerophosphate can be determined using compositions which include all of the other required materials but that under assay.

The assay compositions described herein may, of course, be incorporated into a matrix of absorbent material of the type well known in the art by impregnation or otherwise to yield test compositions suitable for qualitative or semiquantitative assay of glycerol or triglycerides. Typical such materials and elements produced therewith which can be adapted for the assay of glycerol or triglycerides are those described, for example, in the following U.S. Pat. Nos.: 3,092,465, 3,418,099, 3,418,083, 2,893,843, 2,893,844, 2,912,309, 3,008,879, 3,802,842, 3,798,064, 3,298,739, 3,915,647, 3,917,453, 3,933,594, 3,936,357, etc.

The invention has been described in detail with particular reference to certain preferred embodiments thereof, but it will be understood that variations and modifications can be effected within the spirit and scope of the invention.

What is claimed is:

1. A method for quantifying triglycerides in an aqueous liquid comprising the steps of:
   (a) contacting
      (I) a sample of the aqueous liquid and
      (II) enzymes and reagents which effect in the presence of triglyceride-positive liquid an ordered sequence of reactions wherein
         (A) triglycerides are hydrolyzed to glycerol;
         (B) glycerol is converted to L-α-glycerophosphate;
         (C) L-α-glycerophosphate is oxidized by α-glycerophosphate oxidase to produce hydrogen peroxide; and
         (D) the hydrogen peroxide produced in (C) reacts with a substance having peroxidative activity to produce a detectable change; and
   (b) quantitatively detecting the occurrence of said change.

2. The method of claim 1 wherein the detectable change comprises the production of a detectable species formed as a result of said ordered series of reactions.

3. A method for the quantification of triglycerides in an aqueous liquid comprising the steps of:
   (a) contacting in an aqueous medium
      (I) a sample of the aqueous liquid and
      (II) enzymes and reagents which effect in the presence of triglyceride-positive liquid an ordered sequence of quantitative reactions wherein
         (A) triglycerides are hydrolyzed to glycerol;
         (B) glycerol is converted to L-α-glycerophosphate;
         (C) L-α-glycerophosphate is oxidized by α-glycerophosphate oxidase to produce hydrogen peroxide; and
         (D) the hydrogen peroxide produced in (C) reacts with a substance having peroxidative activity to produce a detectable species; and
   (b) quantifying any detectable species produced in (D).

4. A method for the quantification of triglycerides in an aqueous liquid comprising the steps of:
   (a) contacting in an aqueous medium and in the presence of oxygen
      (I) a sample of the aqueous liquid, and
      (II) a reagent composition comprising:
         (A) a lipase;
         (B) glycerol kinase;
         (C) adenosine triphosphate; and
         (D) α-glycerophosphate oxidase and a substance having peroxidative activity, to produce a detectable species; and
   (b) quantitatively detecting the detectable species.

5. A method for the assay of triglycerides in an aqueous liquid comprising the steps of:
   (a) contacting in an aqueous medium and in the presence of oxygen
      (I) a sample of the aqueous liquid, and
      (II) a reagent composition comprising:
         (A) a lipase;
         (B) glycerol kinase;
         (C) adenosine triphosphate;
         (D) α-glycerophosphate oxidase; and
         (E) peroxidase, to produce in the presence of a triglyceride-positive sample a detectable change; and
   (b) quantitatively detecting the occurrence of said change.

6. A method for the assay of triglycerides in an aqueous liquid comprising the steps of:
   (a) contacting in an aqueous medium and in the presence of oxygen
      (I) a sample of the aqueous liquid, and
      (II) a reagent composition comprising:
         (A) lipase;
         (B) glycerol kinase;
         (C) adenosine triphosphate;
         (D) α-glycerophosphate oxidase; and
         (E) an indicator composition comprising a substance having peroxidative activity which produces a detectable product in the presence of hydrogen peroxide; and
   (b) quantifying the occurrence of the detectable product.

7. The method of claim 6 wherein the lipase is a microbial lipase from a source selected from the group consisting of *Rhizopus arrhizus, Candida rugosa,* and *Chromobacterium viscosum*.

8. The method of claim 6 including in the reagent composition with the lipase as an effector either a protease or a compatible surfactant.

9. The method of claim 8 wherein said protease is selected from the group consisting of chymotrypsin, elastase, papain, bromelain and the proteases from *Streptomyces griseus, Aspergillus oryzae* and *Bacillus subtilis*.

10. The method of claim 8 wherein the compatible surfactant is selected from the group consisting of octyl and nonyl phenoxy polyethoxy ethanol.

11. The method of claim 10 wherein the compatible surfactant has an HLB number below about 15 and the number of oxyethylene units in the polyoxyethylene chain is less than 20.

12. The method of claim 6 wherein the glycerol kinase is from *E. coli* or *Candida mycoderma*.

13. The method of claim 6 wherein the α-glycerophosphate oxidase is derived from a microbial source selected from the group consisting of Streptococcaceae and Lactobacillaceae.

14. The method of claim 13 wherein the α-glycerophosphate oxidase is from *Streptococcus faecalis*.

15. The method of claim 14 wherein the *Streptococcus faecalis* is one of the following strains ATCC 11700, ATCC 19634 or ATCC 12755.

16. The method of claim 15 wherein the *Streptococcus faecalis* strain is ATCC 12755.

17. The method of claim 6 wherein the indicator composition also comprises a chromogen which undergoes a detectable change in the presence of hydrogen peroxide and substance having peroxidative activity.

18. The method of claim 17 wherein the substance having peroxidative activity is peroxidase.

19. The method of claim 17 wherein the chromogen comprises a leuco dye which is oxidized to form a colored dye in the presence of hydrogen peroxide and peroxidase.

20. The method of claim 17 wherein the chromogen is oxidizable in the presence of hydrogen peroxide and peroxidase to yield a colorless product which in turn can react to yield a colored product, all in proportion to the amount of hydrogen peroxide present.

21. The method of claim 20 wherein the chromogen composition comprises 4-aminoantipyrine and 1,7-dihydroxynaphthalene.

22. The method of claim 6 wherein the reagent composition is buffered to a pH of between about 6.0 and about 8.0.

23. A method for quantifying triglycerides in blood serum comprising the steps of:
(a) contacting in an aqueous medium and in the presence of oxygen
(I) a sample of the blood serum, and
(II) a composition buffered to a pH of between about 6.0 and about 8.0 and comprising:
(A) lipase;
(B) an effector selected from the group consisting of protease and compatible surfactants;
(C) glycerol kinase from *E. coli* or *Candida mycoderma;*
(D) adenosine triphosphate;
(E) α-glycerophosphate oxidase from *Streptococcus faecalis;*
(F) an indicator composition comprising peroxidase and a chromogen which undergoes a quantifiable color change in the presence of hydrogen peroxide and peroxidase
to produce a quantifiable color change; and
(b) quantitatively detecting said color change.

24. A composition for the quantification of triglycerides in aqueous liquid, the composition comprising:
(a) lipase;
(b) glycerol kinase;
(c) adenosine triphosphate;
(d) α-glycerophosphate oxidase; and
(e) a substance having peroxidative activity.

25. A composition as described in claim 24 wherein the lipase is a microbial lipase from a source selected from the group consisting of *Rhizopus arrhizus, Candida rugosa,* and *Chromobacterium viscosum*.

26. A composition as described in claim 24 including in the reagent composition with the lipase as a hydrolysis stimulator either a protease or a compatible surfactant.

27. A composition as described in claim 26 wherein said protease is selected from the group consisting of chymotrypsin, elastase, papain, bromelain and the proteases from *Streptomyces griseus, Aspergillus oryzae* and *Bacillus subtilis*.

28. A composition as described in claim 26 wherein the compatible surfactant is selected from the group consisting of octyl and nonyl phenoxy polyethoxy ethanol.

29. A composition for the quantification of triglycerides in aqueous liquid comprising:
(a) lipase;
(b) glycerol kinase;
(c) adenosine triphosphate;
(d) α-glycerophosphate oxidase; and
(e) peroxidase.

30. A composition as described in claim 29 wherein the lipase is a microbial lipase from a source selected from the group consisting of *Rhizopus arrhizus, Candida rugosa,* and *Chromobacterium viscosum*.

31. A composition as described in claim 29 further including a protease or a compatible surfactant as a hydrolysis stimulator.

32. A composition as described in claim 31 wherein said protease is selected from the group consisting of chymotrypsin, elastase, papain, bromelain and the proteases from *Streptomyces griseus, Aspergillus oryzae* and *Bacillus subtilis*.

33. A composition as described in claim 31 wherein the compatible surfactant is selected from the group consisting of octyl and nonyl phenoxy polyethoxy ethanol.

34. A composition as described in claim 31 wherein the compatible surfactant has an HLB number below about 15 and the number of oxyethylene units in the polyoxyethylene chain is less than 20.

35. A composition as described in claim 29 wherein the glycerol kinase is from *E. coli* or *Candida mycoderma*.

36. A composition as described in claim 29 wherein the α-glycerophosphate oxidase is derived from a microbial source selected from the group consisting of Streptococcaceae and Lactobacillaceae.

37. A composition as described in claim 36 wherein the α-glycerophosphate oxidase is from *Streptococcus faecalis*.

38. A composition as described in claim 37 wherein the *Streptococcus faecalis* is one of the following strains ATCC 11700, ATCC 19634 or ATCC 12755.

39. A composition as described in claim 38 wherein the *Streptococcus faecalis* strain is ATCC 12755.

40. A composition for the quantification of triglycerides in aqueous liquid comprising:

(a) lipase;
(b) glycerol kinase;
(c) adenosine triphosphate;
(d) α-glycerophosphate oxidase; and
(e) an indicator composition which comprises a substance having peroxidative activity and a chromogen which undergoes a detectable change in the presence of hydrogen peroxide and substance having peroxidative activity.

41. A composition as described in claim 40 wherein the substance having peroxidative activity is peroxidase.

42. A method for quantifying glycerol in aqueous liquid comprising the steps of:
(a) contacting
  (I) a sample of the aqueous solution and
  (II) enzymes and reagents which effect an ordered sequence of reactions wherein
    (A) glycerol is converted to L-α-glycerophosphate;
    (B) L-α-glycerophosphate is oxidized by α-glycerophosphate oxidase to produce hydrogen peroxide; and
    (C) the hydrogen peroxide produced in (B) reacts with a substance having peroxidative activity to produce a detectable change; and
(b) quantitatively detecting the occurrence of said change.

43. The method of claim 42 wherein the detectable change comprises the production of a detectable species formed as a result of said ordered series of reactions.

44. A method for quantifying glycerol in aqueous liquids comprising the steps of:
(a) contacting in an aqueous medium and in the presence of oxygen a sample of the aqueous solution and an ordered sequence of reactions in the presence of glycerol-positive liquid wherein
  (A) glycerol is converted to L-α-glycerophosphate;
  (B) L-α-glycerophosphate is oxidized by α-glycerophosphate oxidase to produce hydrogen peroxide; and
  (C) an indicator composition which comprises a substance having peroxidative activity and a chromogen which undergoes a detectable change in the presence of hydrogen peroxide and substance having peroxidative activity; and
(b) quantifying the detectable change produced in (C).

45. The method of claim 44 wherein the glycerol is converted to L-α-glycerophophate with glycerol kinase from *E. coli* or *Candida mycoderma*.

46. The method of claim 44 wherein the L-α-glycerophosphate oxidase is derived from a micobial source selected from the group consisting of Streptococcaceae and Lactobacillaceae.

47. The method of claim 45 wherein the L-α-glycerophosphate oxidase is from *Streptococcus faecalis.*

48. The method of claim 47 wherein the *Streptococcus faecalis* is one of the following strains ATCC 11700, ATCC 19634 or ATCC 12755.

49. The method of claim 48 wherein the *Streptococcus faecalis* strain is ATCC 12755.

50. The method of claim 44 wherein the substance having peroxidative activity is peroxidase.

51. The method of claim 50 wherein the chromogen comprises a leuco dye which is oxidized to form a colored dye in the presence of hydrogen peroxide and peroxidase.

52. The method of claim 50 wherein the chromogen comprises material which is oxidized in the presence of hydrogen peroxide and peroxidase yielding a colorless product which in turn reacts with other material to yield a colored product in proportion to the amount of hydrogen peroxide present.

53. A composition for the quantification of glycerol in an aqueous liquid comprising:
(a) glycerol kinase;
(b) adenosine triphosphate;
(c) α-glycerophosphate oxidase; and
(d) a substance having peroxidative activity.

54. A composition for the quantification of glycerol in an aqueous liquid comprising:
(a) glycerol kinase;
(b) adenosine triphosphate;
(c) α-glycerophosphate oxidase; and
(d) peroxidase.

55. A composition for the quantification of glycerol in an aqueous liquid comprising:
(a) glycerol kinase;
(b) adenosine triphosphate;
(c) α-glycerophosphate oxidase; and
(d) an indicator composition comprising substance having peroxidative activity and material which undergoes a detectable change in the presence of a peroxide and substance having peroxidative activity.

56. A composition for the quantification of adenosine triphosphate in aqueous solution comprising:
(a) glycerol;
(b) glycerol kinase;
(c) α-glycerophosphate oxidase; and
(d) a substance having peroxidative activity.

57. An element for detecting triglycerides comprising an absorbent material which contains therein:
(a) lipase;
(b) glycerol kinase;
(c) adenosine triphosphate;
(d) α-glycerophosphate oxidase; and
(e) a substance having peroxidative activity.

58. An element for detecting triglycerides comprising an absorbent material which contains therein:
(a) lipase;
(b) glycerol kinase;
(c) adenosine triphosphate;
(d) α-glycerophosphate oxidase; and
(e) an indicator composition comprising a substance having peroxidative activity and a chromogen which undergoes a detectable change in the presence of hydrogen peroxide and substance having peroxidative activity.

59. An element as defined in claim 58 wherein said substance having peroxidative activity is peroxidase.

60. An element for detecting glycerol comprising an absorbent material which contains therein:
(a) glycerol kinase;
(b) adenosine triphosphate;
(c) α-glycerophosphate oxidase; and
(d) an indicator composition comprising a substance having peroxidative activity and material which undergoes a detectable change in the presence of hydrogen peroxide and a substance having peroxidative activity.

61. An element for detecting adenosine triphosphate comprising an absorbent material which contains therein:
(a) glycerol;

(b) glycerol kinase;
(c) α-glycerophosphate oxidase; and
(d) a substance having peroxidative activity.

62. An element for detecting adenosine triphosphate comprising an absorbent material which contains therein:
   (a) glycerol;
   (b) glycerol kinase;
   (c) α-glycerophosphate oxidase; and
   (d) an indicator composition comprising substance having peroxidative activity and material which undergoes a detectable change in the presence of hydrogen peroxide and substance having peroxidative activity.

63. A composition for quantification of glycerol kinase in an aqueous liquid comprising:
   (a) glycerol;
   (b) adenosine triphosphate;
   (c) α-glycerophosphate oxidase; and
   (d) a substance having peroxidative activity.

64. A composition for quantification of lipase in an aqueous liquid comprising:
   (a) triglycerides;
   (b) glycerol kinase;
   (c) adenosine triphosphate;
   (d) α-glycerophosphate oxidase; and
   (e) a substance having peroxidative activity.

65. A composition for quantification of α-glycerophosphate in an aqueous liquid comprising:
   (a) α-glycerophosphate oxidase; and
   (b) a substance having peroxidative activity.

66. An element for detecting glycerol kinase in an aqueous liquid comprising an absorbent material which contains therein:
   (a) glycerol;
   (b) adenosine triphosphate;
   (c) α-glycerophosphate oxidase; and
   (d) a substance having peroxidative activity.

67. An element for detecting lipase in an aqueous liquid comprising an absorbent material which contains therein:
   (a) triglycerides;
   (b) glycerol kinase;
   (c) adenosine triphosphate;
   (d) α-glycerophosphate oxidase; and
   (e) a substance having peroxidative activity.

* * * * *